(12) United States Patent
Chiesi et al.

(10) Patent No.: US 12,031,892 B2
(45) Date of Patent: Jul. 9, 2024

(54) USE OF HOLLOW FIBERS TO OBTAIN BLOOD OR A BLOOD DERIVATIVE IMPOVERISHED FROM BLOOD CELLS AND PLATELETS DERIVED EXTRACELLULAR VESICLES

(71) Applicants: EXOSOMICS S.P.A., Siena (IT); MEDICA S.P.A., Medolla (IT)

(72) Inventors: Antonio Chiesi, Siena (IT); Natasa Zarovni, Siena (IT); Davide Zocco, Siena (IT)

(73) Assignee: Medica S.P.A., Medolla (IT)

(*) Notice: Subject to any disclaimer, the term of this patent is extended or adjusted under 35 U.S.C. 154(b) by 769 days.

(21) Appl. No.: 17/042,349

(22) PCT Filed: Mar. 29, 2019

(86) PCT No.: PCT/EP2019/058028
§ 371 (c)(1),
(2) Date: Sep. 28, 2020

(87) PCT Pub. No.: WO2019/185874
PCT Pub. Date: Oct. 3, 2019

(65) Prior Publication Data
US 2021/0025795 A1 Jan. 28, 2021

(30) Foreign Application Priority Data
Mar. 30, 2018 (EP) ..................................... 18165289

(51) Int. Cl.
G01N 1/40 (2006.01)
B01D 69/08 (2006.01)
B01D 71/68 (2006.01)

(52) U.S. Cl.
CPC ........... *G01N 1/4005* (2013.01); *B01D 69/08* (2013.01); *B01D 71/68* (2013.01); *B01D 2325/02834* (2022.08); *G01N 2001/4016* (2013.01)

(58) Field of Classification Search
CPC .............................. G01N 1/4005; B01D 69/08
See application file for complete search history.

(56) References Cited

U.S. PATENT DOCUMENTS

2018/0369460 A1  12/2018  Bonn

FOREIGN PATENT DOCUMENTS

| EP | 3093032 A1 | 11/2016 | |
|---|---|---|---|
| WO | 0182958 A3 | 11/2001 | |
| WO | 2007127848 A1 | 11/2007 | |
| WO | 2015130956 A3 | 9/2015 | |
| WO | WO-2016181300 A1 * | 11/2016 | ....... A61F 13/00068 |
| WO | WO-2017136430 A1 * | 8/2017 | ....... B01L 3/502715 |

OTHER PUBLICATIONS

International Search Report and Written Opinion for International Patent Application No. PCT/EP2019/058028, mailed May 31, 2019, 12 pages.
Hackstein et al., Prospective quality control study of a novel gravity-driven whole blood separation system suitable for humanitarian crises, Vox Sanguinis, Nov. 1, 2017, pp. 806-809, vol. 112, No. 8, International Society of Blood Transfusion.
Black et al., Platelet-derived extracellular vesicles in plateletpheresis concentrates as a quality control approach, Transfusion, Blood Components, Sep. 2015, pp. 2184-2196, vol. 55, No. 9, AABB, USA.
Ishihara et al., Protein Adsorption-Resistant Hollow Fibers for Blood Purification, Artificial Organs, Dec. 11, 2002, pp. 1014-1019, vol. 26, No. 12, International Society for Artificial Organs, Blackwell Publishing, Inc., USA.
Van Der Pol et al., Classification, Functions, and Clinical Relevance of Extracellular Vesicles, Pharmacological Reviews, Jul. 1, 2012, pp. 676-705, vol. 64, No. 3, The American Society for Pharmacology and Experimental Therapeutics, USA.
Mock I. Jr., Hollow-Fiber Membranes, Membrane Processes, vol. I, Encyclopedia of Desalination and Water Resources, 9 pages provided.
Zhang et al., Identification of distinct nanoparticles and subsets of extracellular vesicles by asymmetric flow field-flow fractionation, Nature Cell Biology, Mar. 2018, pp. 332-343, vol. 20, No. 3, Macmillan Publishers Limited, Springer Nature.
Lozupone et al., The human homologue of Dictyostelium discoideum phg1A is expressed by human metastatic melanoma cells, EMBO Reports, Dec. 2009, pp. 1348-1354, vol. 10, No. 12, European Molecular Biology Organization.
Lozupone et al., TM9SF4 is a novel V-ATPase-interacting protein that modulates tumor pH alterations associated with drug resistance and invasiveness of colon cancer cells, Oncogene, Oct. 1, 2015, pp. 5163-5174, vol. 34, No. 40, Macmillan Publishers Limited, Springer Nature.
Paolillo et al., Human TM9SF4 Is a New Gene Down-Regulated by Hypoxia and Involved in Cell Adhesion of Leukemic Cells, PLOS One, May 11, 2015, p. e0126968, vol. 10, No. 5, PLOS, USA.
De Haene et al., Comparison of triglyceride concentration with lipemic index in disorders of triglyceride and glycerol metabolism, Clinical Chemistry and Laboratory Medicine, Feb. 2006, pp. 220-222, vol. 44, No. 2, Walter de Gruyter.
Pak et al., Preparation of Cellulose Acetate Hollow-Fiber Membranes for C02/CH4 Separation, Environmental Engineering Science, 2015, vol. 33, No. 1, Original Article, Mary Ann Liebert, Inc., 8 pages.
Yang et al., Performance improvement of PVDF hollow fiber-based membrane distillation process, Journal of Membrane Science, Mar. 1, 2011, pp. 437-447, vol. 369, No. 1-2, Science Direct, Elsevier B.V.

(Continued)

*Primary Examiner* — Allison M Fox
*Assistant Examiner* — Jennifer S Spence
(74) *Attorney, Agent, or Firm* — Armstrong Teasdale LLP

(57) ABSTRACT

A method is provided for using hollow fibers having a porosity above 20 nm, in particular polyethersulfone hollow fibers, to impoverish blood and blood-derivatives from blood-derived extracellular vesicles, in particular exosomes and exomers. Methods for obtaining and analyzing the impoverished samples are also provided.

10 Claims, 10 Drawing Sheets
Specification includes a Sequence Listing.

(56) References Cited

OTHER PUBLICATIONS

Zhu et al., Preparation and properties of PTFE hollow fiber membranes for desalination through vacuum membrane distillation, Journal of Membrane Science, Nov. 1, 2013, pp. 145-153, vol. 446, Science Direct, Elsevier B.V.

Dashti et al., Recent Progresses in Ceramic Hollow-Fiber Membranes, ChemBioENg Reviews, Feb. 2015, pp. 1-17, vol. 2, Issue 1, Wiley-VCH Verlag GmbH & Co. KGaA, Weinheim, DE.

Qiu et al., Cross-linked PVC/hyperbranched polyester composite hollow fiber membranes for dye removal, Reactive and Functional Polymers, Jan. 2018, pp. 51-59, vol. 122, Science Direct, Elsevier B.V.

Li et al., Polyethyleneimine-Functionalized Polyamide Imide (Torlon) Hollow-Fiber Sorbents for Post-Combustion C02 Capture, ChemSusChem, Jul. 2013, pp. 1216-1223, vol. 6, No. 7, Wiley-VCH Verlag GmbH & Co. KGaA, Weinheim, DE.

Labreche et al., Poly(amide-imide)/silica supported PEI Hollow Fiber Sorbents for Postcombustion CO2 Capture by RTSA, ACS Applied Materials & Interfaces, Nov. 12, 2014, pp. 19336-19346, vol. 6, No. 21, ACS Publications, USA.

Zhang et al., Autohydrogenotrophic denitrification of drinking water using a polyvinyl chloride hollow fiber membrane biofilm reactor, Journal of Hazardous Materials, Oct. 15, 2009, pp. 203-209, vol. 170, No. 1, Science Direct, Elsevier B.V.

Higa et al., Preparation of PVA-Based Hollow Fiber Ion-Exchange Membranes and Their Performance for Donnan Dialysis, Membranes, Jan. 2, 2019, 9010004, vol. 9, No. 1, MDPI, Basel, CH.

\* cited by examiner

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: BRAFwt (forward primer)

<400> SEQUENCE: 1
taggtgattt tggtctagct acagt                                              25

<210> SEQ ID NO 2
<211> LENGTH: 24
<212> TYPE: DNA
<213> ORGANISM: Artificial Sequence
<220> FEATURE:
<223> OTHER INFORMATION: BRAFwt (reverse primer)

<400> SEQUENCE: 2
ttaatcagtg gaaaatagc ctca                                                24

<210> SEQ ID NO 3
<211> LENGTH: 25
<212> TYPE: DNA
<213> ORGANISM: Artificial Sequence
<220> FEATURE:
```

-continued

```
<223> OTHER INFORMATION: BRAF V600E (forward primer)

<400> SEQUENCE: 3
taggtgattt tggtctagct acaga                                    25

<210> SEQ ID NO 4
<211> LENGTH: 24
<212> TYPE: DNA
<213> ORGANISM: Artificial Sequence
<220> FEATURE:
<223> OTHER INFORMATION: BRAF V600E (reverse primer)

<400> SEQUENCE: 4
ttaatcagtg gaaaaatagc ctca                                     24

<210> SEQ ID NO 5
<211> LENGTH: 38
<212> TYPE: DNA
<213> ORGANISM: Artificial Sequence
<220> FEATURE:
<223> OTHER INFORMATION: Probe

<400> SEQUENCE: 5
ccgaagggga tccagacaac tgttcaaact gccttcgg                      38
```

USE OF HOLLOW FIBERS TO OBTAIN BLOOD OR A BLOOD DERIVATIVE IMPOVERISHED FROM BLOOD CELLS AND PLATELETS DERIVED EXTRACELLULAR VESICLES

CROSS-REFERENCE TO RELATED APPLICATIONS

This application is a National Stage Application of International Patent Application No. PCT/EP2019/058028, having an International Filing Date of Mar. 29, 2019, which claims the benefit of priority to European Patent Application No. 18165289.2, filed Mar. 30, 2018, the entire contents of which are hereby incorporated by reference herein.

FIELD OF THE INVENTION

The present invention relates to the use of hollow fibers having a porosity above 20 nm, in particular polyethersulfone hollow fibers, to impoverish blood and blood-derivatives from blood-derived extracellular vesicles, in particular microvesicles and exosomes and exomers, and to methods for obtaining and analysing such impoverished samples.

BACKGROUND TO THE INVENTION

Extracellular vesicles are 30 nm-2 μm membranous entities of cellular origin. These comprise apoptotic bodies (above 1 μm), oncosomes (above 1 μm), microvesicles (200 nm-1 μm), exosomes (30-120 nm) and exomers (around 35 nm) (Van Der Pol et al., Zhang et al.).

Hollow fibers (HF) are a class of semipermeable barriers that are of use in particular in the field of dialysis (Ishihara et al.). Their main characteristic is their porosity, i.e. the average pore diameter and pore distribution. In the filed of medicine, they are typically used as filters for hemodialysis, hemofiltration, and plasmapheresis.

Hollow fibers have been produced using a variety of materials including cellulose, cellulose ester, polysulfone, polyethersulfone (PES), polymethylmetacrilate (PMMA), polyamide, nitrogen-containing polymers, glass, silica, cellulose acetate, polyvinyldene fluoride (PVDF), poly (vinyl chloride) (PVC), polytetrafluoroethylene (PTFE), poly ester, ceramic, polyimide, polyetherimide, polyethyleneimine-functionalized polyamide imide (Torlon™), poly (vinyl alcohol) (PVA). (Seo-Hyun Pak et al.; Xing Yanga et al. Hailin Zhu et. Al; Amir Dashti et al.; Ze-Lin Qiu et al.; Li F S et al.; Labreche Y et al.; Zhang Y et al.; Higa M et al., Mock 2007).

The art is laden with examples of how blood and blood derivatives can be prepared for analysis.

The preparation of blood derivatives typically suffers from activation of platelets and white blood cells and hemolysis. The activation of platelets, for example, can be achieved by merely shaking a tube test containing a blood sample (Black et al.). Also, the presence of extracellular vesicles of hematopoietic origin is a known confounding factor for the isolation and molecular analysis of parenchymal and stromal-derived extracellular vesicles, affecting signal-to-noise ratio of the analysis and the reproducibility of the results.

PRIOR ART

Hollow fibers have been described in the prior art in connection with their ability to retain vesicles either because their porosity does not allow their passage (WO2007127848, WO2001082958) or because the hollow fibers have been chemically modified in order to bind the vesciles (WO2015130956).

DETAILED DESCRIPTION OF THE INVENTION

Figure 1:
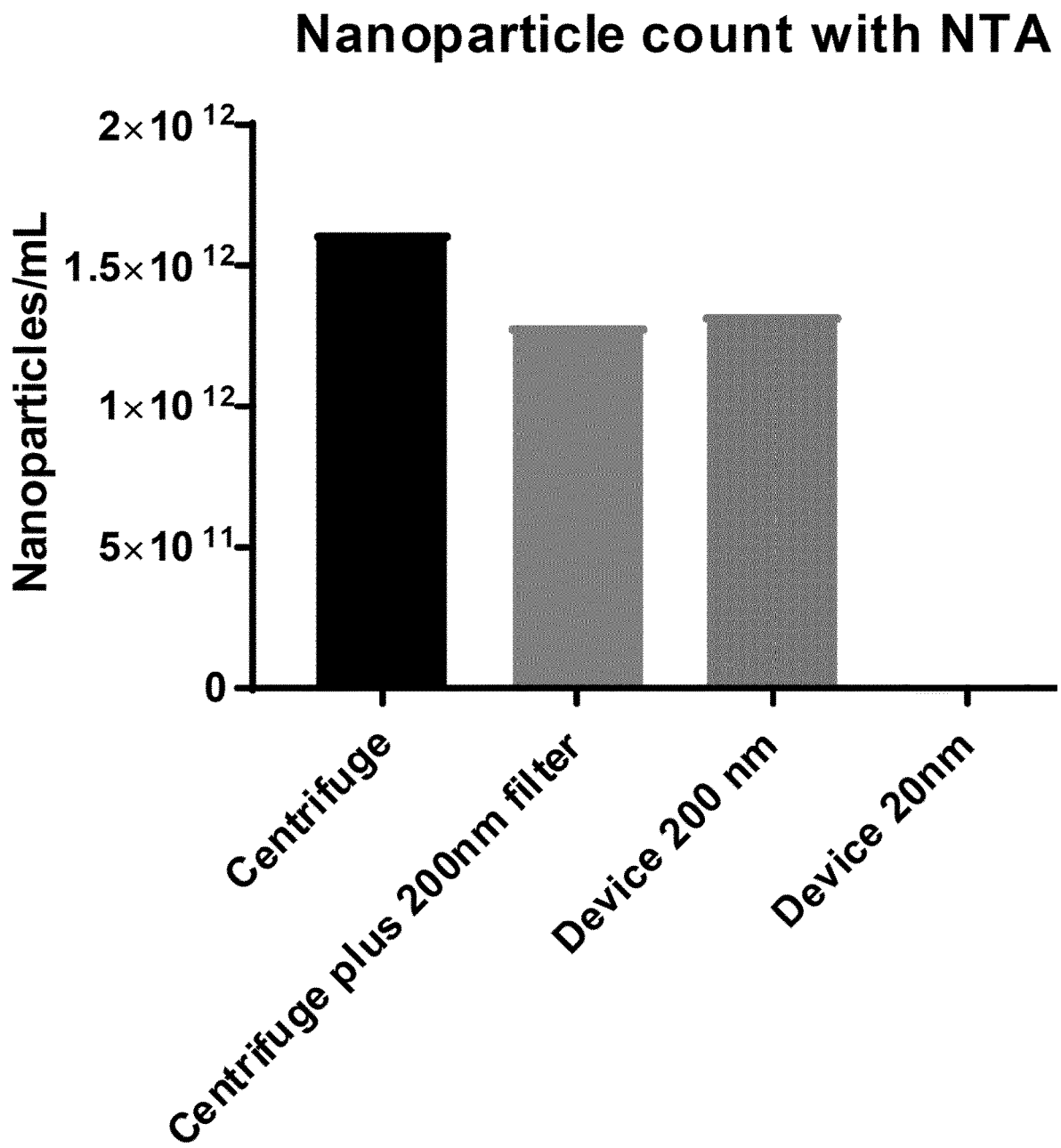
FIG. 1—Nanoparticle count of plasma obtained by centrifugation, by filtration through a 200 nm porosity HF device or by filtration through a 20 nm porosity HF device.

We have surprisingly found that the use of hollow fibers filters having a porosity of above 20 nm by gravity filtering allows for an impoverishment from extracellular vescicles originating from certain blood components and having a size that is inferior to the porosity of the hollow fibers.

In a first aspect of this invention, there is provided the in vitro use of hollow fibers having a porosity above 20 nm to impoverish, by gravity filtering, a blood or blood-derived liquid sample from extracellular vesicles, such extracellular vesicles having a size that is inferior to the porosity of the hollow fibers and originating from blood components selected from the group consisting of blood red cells, blood white cells, platelets and combinations thereof.

In a second aspect to this invention, there is provided an in vitro method for obtaining blood or a blood derivative substantially impoverished in extracellular vesicles originating from blood components selected from the group consisting of red blood cells, white blood cells, platelets and any combination thereof, the method including the steps of gravity filtering a blood or blood-derived liquid sample through a filter comprising hollow fibers having a porosity above 20 nm, thereby obtaining blood or a blood derivative substantially impoverished in extracellular vesicles, such extracellular vesicles having a size that is inferior to the porosity of the hollow fibers.

In a third aspect to this invention, there is provided an in vitro method to analyse the extracellular vesicles content of a blood or blood-derived liquid sample, such method including:
  a) gravity-filtering the blood or blood-derived liquid sample through a hollow fibers filter having a porosity above 20 nm, thereby obtaining a filtrate,
  b) analysing the extracellular vesicles content of the filtrate obtained in step a).

The skilled man will know which analysis to perform and on how to perform it, depending on the circumstances and on the basis of his own experience and the literature available in the field. Such analysis may for example be directed at measuring the quantities of extracellular vesicles that harbor a particular protein at their surface using an enzyme-linked immunosorbent assay (ELISA) or flow cytometry (FACS). Other analyses may be directed at counting the number of total nanoparticles in the sample via nanotracking analysis (NTA) or measuring gene expression by quantitative real time polymerase chain reaction (qRT-PCR) or next generation sequencing (NGS).

In an embodiment under any aspect of this invention, the hollow fibers comprise polyethersulfone hollow fibers.

In an embodiment under any aspect of this invention, the hollow fibers consist of polyethersulfone hollow fibers.

In an embodiment under any aspect of this invention, the hollow fibers comprise a material chosen from the list of cellulose, cellulose ester, polysulfone, polyethersulfone (PES), polymethylmetacrilate (PMMA), polyamide, nitrogen-containing polymers, glass, silica, cellulose acetate, polyvinyldene fluoride (PVDF), poly (vinyl chloride) (PVC), polytetrafluoroethylene (PTFE), poly ester, ceramic, polyimide, polyetherimide, polyethyleneimine-functionalized polyamide imide (Torlon™) and poly (vinyl alcohol) (PVA).

In an embodiment under any aspect of this invention, the hollow fibers consist in a material chosen from the list of cellulose, cellulose ester, polysulfone, polyethersulfone (PES), polymethylmetacrilate (PMMA), polyamide, nitrogen-containing polymers, glass, silica, cellulose acetate, polyvinyldene fluoride (PVDF), poly (vinyl chloride) (PVC), polytetrafluoroethylene (PTFE), poly ester, ceramic, polyimide, polyetherimide, polyethyleneimine-functionalized polyamide imide (Torlon™) and poly (vinyl alcohol) (PVA).

In an embodiment under any aspect of this invention, the porosity is selected from the list of above 20 nm, above 25 nm, above 30 nm, above 35 nm, above 40 nm, above 45 nm, above 50 nm, above 55 nm, above 60 nm, above 65 nm, above 70 nm, above 75 nm, above 80 nm, above 85 nm, above 90 nm, above 95 nm, above 100 nm, above 105 nm, above 110 nm, above 115 nm, above 120 nm, above 125 nm, above 130 nm, above 135 nm, above 140 nm, above 145 nm, above 150 nm, above 155 nm, above 160 nm, above 165 nm, above 170 nm, above 175 nm, above 180 nm, above 185 nm, above 190 nm, above 195 nm and above 200 nm.

In an embodiment under any aspect of this invention, the porosity is below 500 nm.

In an embodiment under any aspect of this invention, the porosity is selected from the list of about 150 nm, about 200 nm, about 250 nm, about 300 nm, about 350 nm, about 400 nm, about 450 nm, about 500 nm and any interval comprising these values.

In an embodiment under any aspect of this invention, the porosity is selected from the list of 150 nm, 200 nm, 250 nm, 300 nm, 350 nm, 400 nm, 450 nm, 500 nm and any interval comprising these values.

In an embodiment under any aspect of this invention, the hollow fibers have a porosity selected from the group of ranges consisting of about 150 to about 250 nm, about 150 to about 300 nm, about 150 to about 350 nm, about 150 to about 400 nm, about 150 to about 450 nm, about 150 to about 500 nm, about 200 to about 250 nm, about 200 to about 300 nm, about 200 to about 350 nm, about 200 to about 400 nm, about 200 to about 450 nm and about 200 to about 500 nm.

In an embodiment under any aspect of this invention, the hollow fibers have a porosity selected from the group of ranges consisting of 150 to 250 nm, 150 to 300 nm, 150 to 350 nm, 150 to 400 nm, 150 to 450 nm, 150 to 500 nm, 200 to 250 nm, 200 to 300 nm, 200 to 350 nm, 200 to 400 nm, 200 to 450 nm and 200 to 500 nm.

In an embodiment under any aspect of this invention, the hollow fibers have a porosity of about 200 nm.

In an embodiment under any aspect of this invention, the hollow fibers have a porosity equal to 200 nm.

In an embodiment under any aspect of this invention, the blood-derived liquid sample is a plasma sample.

In an embodiment under any aspect of this invention the extracellular vesicles are selected from the group consisting of microvesicles, exosomes, exomers and combinations thereof.

All embodiments may be combined to generate new embodiments under any of the above aspects of the invention.

EXAMPLES

The invention is now described by means of non-limiting examples.

Materials & Methods

A) Blood Collection

All patients had been fasting since midnight before blood collection in the morning. The blood was either collected in a blood bag containing CPD (CompoFlow; Fresenius Kabi) or collected in K2-EDTA tubes for plasma (VACUTAINER® Becton Dickinson, purple cap, REF 367864, 6.0 ml). K2-EDTA tubes were subsequently inverted 5 or 6 times, kept in a vertical position and stored at room temperature (20-25° C.) until further processing.

B) Plasma Preparation by Centrifuge

Plasma preparation by centrifuge was performed within an hour from collection by centrifugation of whole blood at 1500 g for 10 minutes at 20-25° C. The plasma was collected using a disposable Pasteur pipette (Steroglass, REF: LPMW032653; 5 ml), avoiding to resuspend it by stopping 3-4 mm above the buffy coat. Samples were visually checked for traces of lipids, bile (Itterum) or hemolysis. Plasma was collected in 15 mL Falcon tubes, gently inverted, and aliquoted in labeled cryotubes (Cat. Num: n° BSM 535, Biosigma) and stored at −20° C.

C) Plasma Obtained Through Filtration of 200 nm Porosity Non-HF Cellulose Filter Plasma was prepared by centrifugation as previously described and filtered through a 200 nm porosity non-HF cellulose filter (Cat. Num: 190-9920; Nalgene). The filtered plasma was collected in a 15 mL Falcon Tube, aliquoted in 2 mL microcentrifuge tubes and stored at −20° C. prior further use.

D) Plasma Obtained Through Filtration of 20/200 nm Porosity Polyethersulfone Hollow Fiber Devices Plasma was obtained using modified versions of commercially available polyethersulfone hollow fiber device with 20 nm or 200 nm porosity, commonly used for hemodialysis (Plasmart 50; Medica Sr, Italy). The device was modified by reducing its length from 150 mm to 60 mm, thus lowering the volume of blood required for priming. Briefly, one of the two side outlets were connected to the whole blood bag or K2-EDTA tube while the outlet at the opposite side of the device was connected to an empty bag. A third lateral outlet was connected to an empty bag for collection of the filtrated plasma. The blood bag was left at RT for at least 30 minutes and gently mixed prior to use.

Forty milliliters of whole blood were filtrated through the device by gravity filtration and 15 mL (30%) of plasma were collected in the lateral bag, transferred to a 50 mL Falcon tube, aliquoted in 2 mL microcentrifuge tubes and stored at −20° C. Whole blood and its cellular components were concentrated in the retentate, collected in the side bag and discarded.

E) Nanoparticle Tracking Analysis (NTA)

Prior to analysis, plasma samples were centrifuged at 13000 g to eliminate larger vesicles that might affect the analysis and further diluted 1:10000 with PBS. NTA was performed using an LM10 Nanosight instrument (Malvern, UK) setting camera level at 16 and slider shutter at 13000. Particle concentration was calculated as average of three independent measurements.

F) Exosome Quantification by ELISA

Plasma samples were thawed at RT and 1 µL of protease inhibitor cocktail (1000×; Sigma Cat Num: P-834) was added to each sample to preserve protein biomarkers. Plasma samples were centrifuged at 1200 g for 20 minutes at room temperature (RT) to eliminate residual red blood cells and cellular debris. The resulting supernatant was collected and diluted in a volume ratio 1:1 of phosphate buffer (PBS).

Briefly, 100 µl of diluted plasma were incubated overnight at 4° C. in 96 well plates pre-coated with 0.1 µg/well of anti-CD9 antibody (Cat Num: HBM-CD9-100, HansaBioMed Life Sciences Ltd), anti-CD45 antibody (Cat Num: 610265, BD), anti-CD61 antibody (Cat Num: 555752, BD); anti-CD235 antibody (Cat Num: 555569, BD) and anti-TM9SF4 antibody (2 µg/ml). After three washes with washing buffer (PBS-Tween 0.05%), plates were incubated with biotinylated anti-CD9 antibody (Cat Num: 558749, BD Pharmigen), incubated for 2 hrs at 4° C., washed thrice with washing buffer, incubated for one hour at 4° C. with matched poly-HRP-streptavidin secondary antibody (Cat Num: 21140, Pierce) and washed thrice with washing buffer. Colorimetric reaction was started by adding 100 µl of Substrate Solution (TMBlue POD; 1:1 solution A and B, Pierce) to each well, incubating 10 minutes in the dark at RT and stopped by adding 100 µl of stop solution (1N sulfuric acid). The O/D adsorbance is read with a M1000 Tecan at 450 nm and results were expressed as Signal to Background (StB) ratio.

G) Preparation of Microvesicle Pellet

Centrifuge-obtained plasma and hollow-fiber-filtered plasma were further centrifuged at 10000 g for 30 minutes at RT to obtain microvesicle (MV) pellet. MV pellet was resuspended in 100 □L of PBS before further processing.

H) Extraction of Small RNA from MV Pellet and Electropherogram Analysis

RNA was extracted from MV pellets using the Overall Exosome Immunocapture and RNA extraction kit from human biofluids and cell media (Cat Num: HBM-RNA-BOF-20; HansaBioMed Life Sciences Ldt, Estonia) and eluted in 15 mL of elution buffer according to the manufacturer's instructions. Five microliters of extracted RNA were loaded onto a RNA 6000 Pico Kit (Cat Num: 5067-1513; Agilent Technologies) and run on a Bioanalyzer instrument to obtain an RNA electropherogram.

I) Spiking Blood Samples with $BRAF^{V600E}$-Positive Tumor Exosomes and Isolation of Exosome-Associated DNA Ten milliliters of whole blood from healthy donor patients were spiked with 80 µl of $BRAF^{V600E}$-positive tumor exosomes purchased from a commercial supplier (5.5 µl/µl, COLO1 cell line, HansaBioMed Life Sciences Ldt).

Exosome-associated DNA (Exo-DNA) from spiked tumor exosomes was extracted and purified using a commercially available kit for circulating DNA extraction (seleCTEV™ low input DNA; Exosomics Siena Spa, Italy). Briefly, exosomes were captured from plasma using a proprietary peptide and pelleted down after a 2-hour incubation. Exosome pellets were lysed with a proprietary lysis buffer and digested with proteinase K to release the DNA from protein complexes. The sample was then supplemented with ethanol, loaded onto a silica membrane spin column and centrifuged at 10000 g for 1 minute. Following centrifugation, the flow-through was discarded. Two washing steps were performed according to the manufacturer's instructions to get rid of contaminating solvents and plasma-derived inhibitors before elution. Exo-DNA was eluted in 50 µl of elution buffer and stored at −20° C. before use.

Amplification of $BRAF^{V600E}$ and $BRAF^{WT}$ genes by qPCR

Each qPCR reaction included 10 µl of purified Exo-DNA, 1×SsoAdvanced Universal Probes Mastermix (Biorad; US), 0.625 µl of primers (10 µM) and 0.3125 µl of fluorescent probe (10 µM) in a total volume of 25 µl. The following primer and probes were used:

```
a) BRAF^WT FW:
TAGGTGATTTTGGTCTAGCTACAG+T;

b) BRAF^WT RW:
TTAATCAGTGGAAAAATAGCCTCA;

c) BRAF^V600E FW:
TAGGTGATTTTGGTCTAGCTACAG+A;

d) BRAF^V600E RW
TTAATCAGTGGAAAAATAGCCTCA e) Probe: 5'-FAM
CCGAAGGGGATC+CAGACAA+CTGTTCAAACTGCCTTCG

G-3BHQ1-3
```

After careful mixing, each reaction was loaded in triplicate on a 96-well PCR plate and the following qPCR program was launched: 95° C. for 3, 40 cycles at 95° C. for 5" and 60° C. for 30", followed by a final hold step at 4° C. To calculate the % of recovered BRAF$^{V600E}$ the following formula was used:=$2^{\wedge(Ct_{input}-Ct_{isolation})}$]%.

L) Detection of BRAF$^{V600E}$ gene copies by digital droplet PCR

Each digital droplet PCR reaction included 10 µl of purified Exo-DNA, 2× of ddPCR Supermix for Probes (Cat. Num 186301; Biorad), 20× of Mutation Detection Assay for BRAF V600E (assay ID: dHsaMDV2010027; Biorad) and 5 µl of DNase-free water. Each reaction was loaded according to the manufacturer's instructions and the the following ddPCR program was launched: 95° C. for 10', 40 cycles at 95° C. for 30" and 56° C. for 1', followed by a final hold step at 4° C. BRAF V600E gene copies and allelic frequencies were calculated using the QuantaSoft Software (Biorad).

M) Quantification of Lipemic Index of Plasma Samples

Lipemic index was measured from 500 ul of plasma using the Serum Index Gen.2 kit on a Cobas instrument according to the manufacturer's instructions (Cat. Num. 05172179190; Roche).

Example 1: Hollow Fiber-(HF)-Device with 200 nm Pores Efficiently Separates Nanoparticle-Rich Plasma from Blood FIG. 1. Depicts the nanoparticles count with nanotracking analysis (NTA) of plasma obtained from whole blood using either a centrifuge, a centrifuge plus a 200 nm non-HF cellulose filter, a polyethersulfone hollow fiber filter of 200 nm porosity or 20 nm porosity.

It is thus shown that the method of the invention allows to obtain a similar nanoparticles count as the centrifuge plus non-HF cellulose filter.

Figure 2:
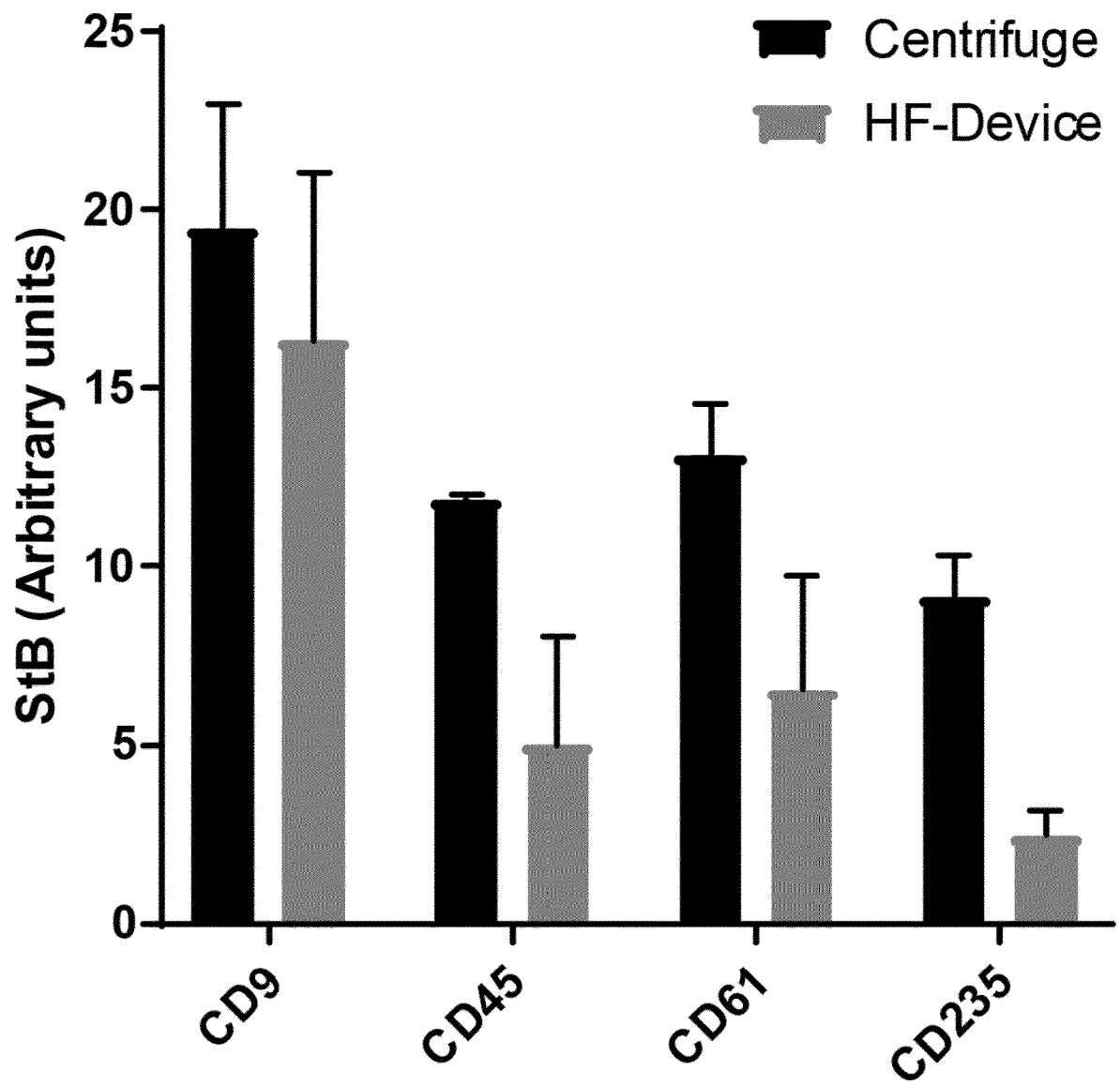
FIG. 2—Quantities of blood derived exosomes measured in plasma samples obtained by filtration through a 200 nm HF device or by the allelic frequency BRAF gene copies (copies/mL) in the plasma of three metastatic melanoma patient centrifugation.

Example 2: Plasma Obtained from the 200 nm HF Filtering of Whole Blood has Less Red and White Blood-Cell Derived Extracellular Vesicles than Centrifuge-Obtained Plasma FIG. 2 depicts the quantities of extracellular vesicles captured from healthy donor plasma obtained either by centrifugation or filtration through a 200 nm porosity polyethersulfone HF device using an anti-CD9 antibody (generic EV marker), an anti-CD45 antibody (generic white blood cell marker), an anti-CD61 antibody (generic platelet marker) or an anti-CD235 antibody (generic erythrocyte marker).

It is thus shown, that the use of a 200 nm porosity polyethersulfone HF device impoverishes the sample from extracellular vesicles derived from either white blood cells, red blood cells and platelets.

Figure 3:
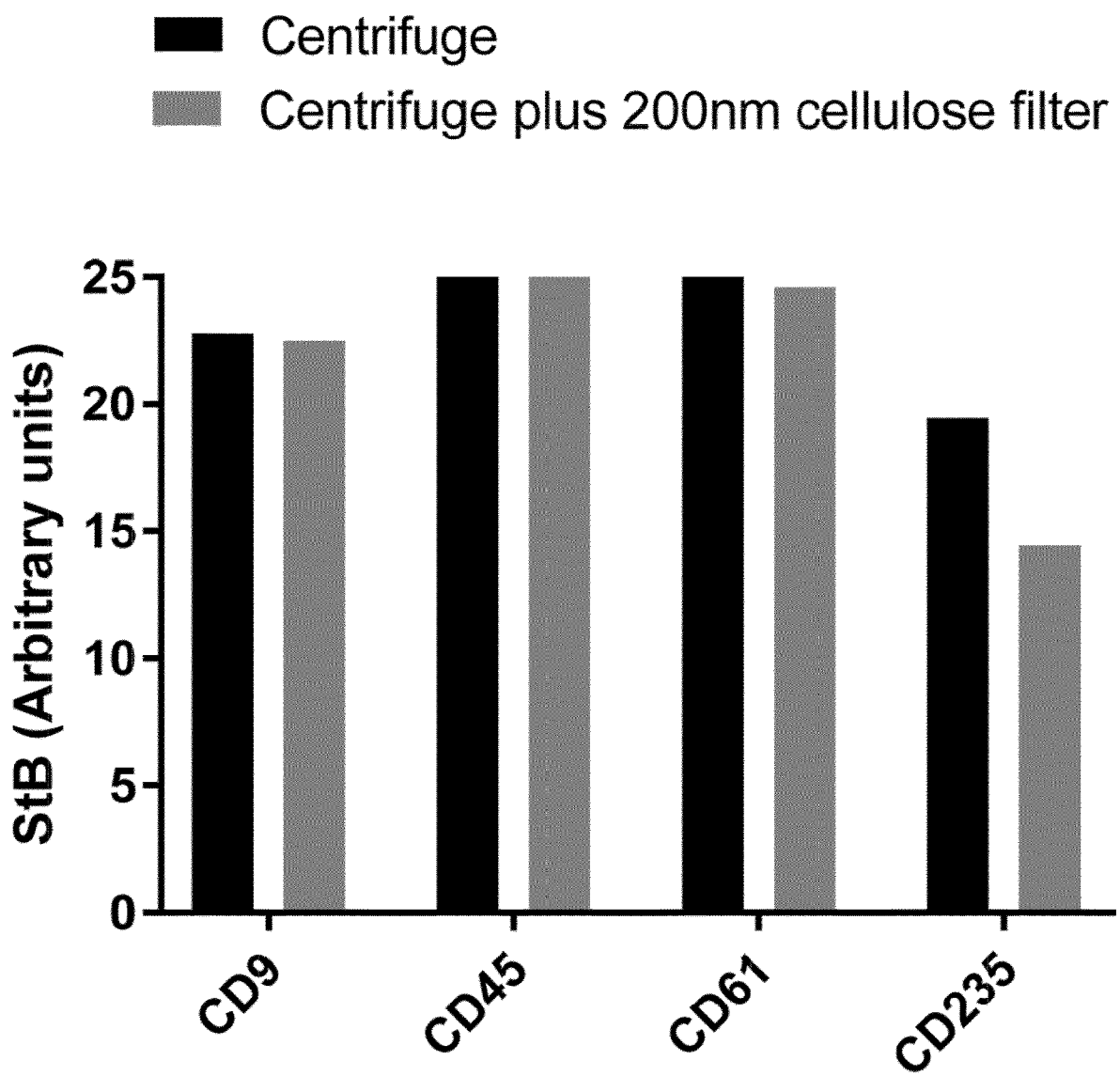
FIG. 3—Quantities of blood derived exosomes measured in plasma samples obtained by filtration through a 200 nm-porosity non-HF cellulose filter.

Example 3: A 200 nm Non-HF Cellulose Filter Cut Off does NOT Select Extracellular Vesicle Subpopulations FIG. 3 depicts the quantities of extracellular vesicles captured from plasma obtained either by centrifugation or filtration through a 200 nm non-HF cellulose filter using an anti-CD9 antibody (generic EV marker), an anti-CD45 antibody (generic white blood cell marker), an anti-CD61 antibody (generic platelet marker) or an anti-CD235 antibody (generic erythrocyte marker).

It is thus shown, that such filter does not impoverish the sample from extracellular vesicles derived from either white blood cells, red blood cells and platelets.

Example 4: The 200 nm HF Device Truly Selects for Particles Below this Size

Figure 4:
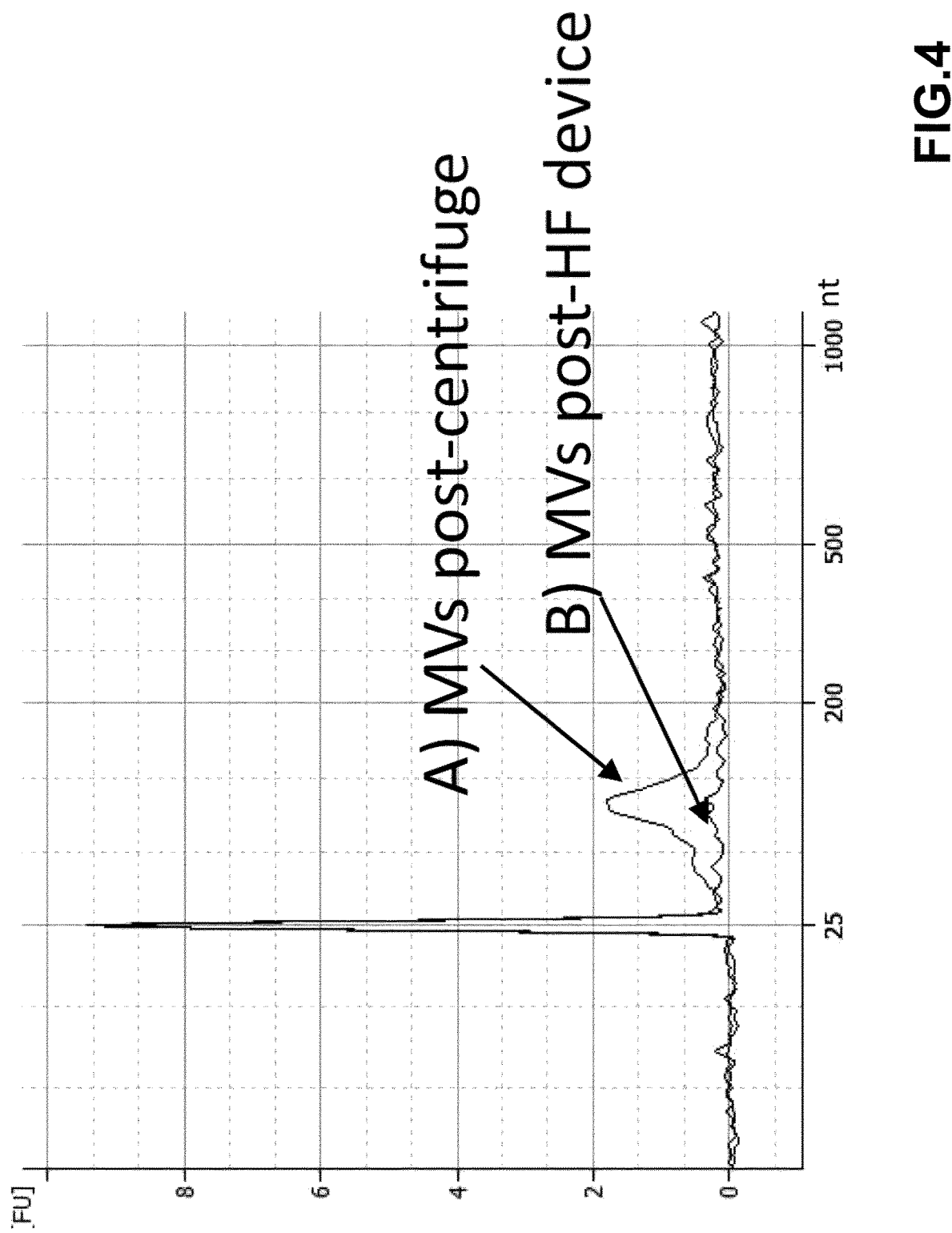
FIG. 4—Small RNA electropherogram of microvesicles present in plasma samples obtained by filtration through a 200 nm HF device or centrifugation.

FIG. 4 depicts the small RNA electropherogram of microvesiles obtained in (A) a plasma sample obtained by centrifugation of whole blood and (B) a plasma sample obtained by filtration of whole blood through a 200 nm porosity polyethersulfone HF device.

These data show that the plasma obtained by by filtration through the HF device is depleted from certain microvesicles that are present in plasma obtained by centrifugation. These microvesicles are known from the literature for being larger than 200 nm (Van der Pol et al.), hence the 200 nm porosity truly selects for particles below this size.

Figure 5:
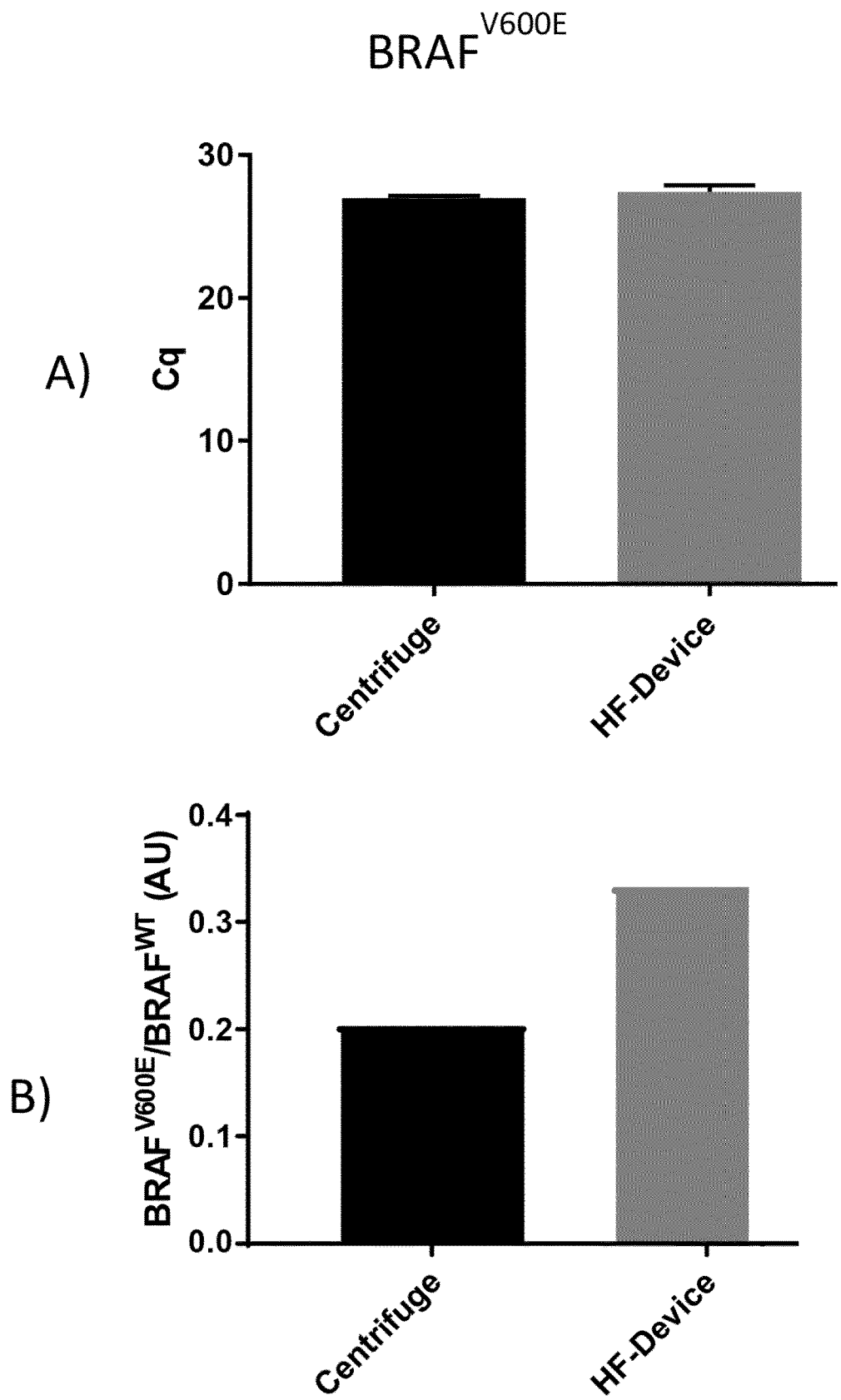
FIG. 5—Levels of $BRAF^{V600E}$ mutation (A) or the ratio of $BRAF^{V600E}$ vs $BRAF^{WT}$ (B) in tumour exosomes spiked in healthy donor blood as measured after either centrifugation or filtering through 200 nm polyethersulfone HF device.

Example 5: BRAF$^{V600E}$ Positive-Tumor Exosomes are Efficiently Recovered in the Plasma Obtained from Whole Blood after Filtration with a 200 nm HF Device FIG. 5 depicts the levels of BRAF$^{V600E}$ mutation (A) or the ratio of BRAF$^{V600E}$ vs BRAF$^{WT}$ (B) in tumour exosomes as measured after either centrifugation or filtering through 200 nm polyethersulfone HF device, of a whole blood sample which has been spiked with such tumour exosomes as described above in the material and methods.

It is there shown that the method of the invention does not significantly alter the levels of tumour exosomes found in a plasma sample with respect to the classic centrifugation method.

Moreover, the difference in FIG. 5B highlights how the method of invention reduces the level of BRAF$^{WT}$ as a consequence of the impoverishment in BRAF$^{WT}$-bearing extracellular vesicles.

Example 6: HF-Filtering with 200 nm Porosity Eliminates False Positive Signal of the Metabolic Marker TM9SF4

Figure 6:
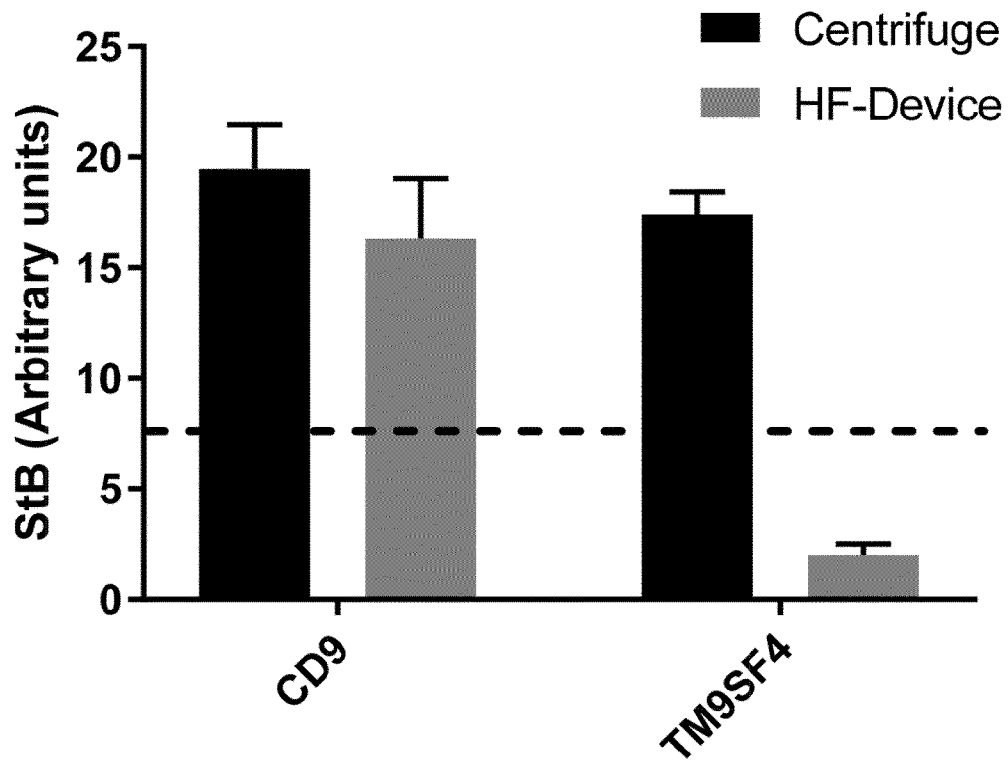
FIG. 6—Quantities of CD9- and TM9SF4-positive exosomes measured in plasma samples obtained by filtration through a 200 nm HF device or by centrifugation.

FIG. 6 depicts the quantities of exosomes captured from healthy donor plasma obtained either by centrifugation or filtration through a 200 nm porosity polyethersulfone HF device using an anti-CD9 antibody (generic EV marker) or an anti-TM9SF4 antibody (metabolic marker expressed on exosomes derived from both tumor parenchymal and stromal cells undergoing glycolytic switch (Lozupone et al. 2009; Lozupone et al. 2015) but also from activated hematopoietic cells (Paolillo et al).

It is shown that the levels of TM9SF4 positive exosomes from healthy donor plasma obtained with the method of invention are below the diagnostic threshold (dotted line) set for positive detection. Conversely, levels of TM9SF4 positive exosomes from healthy donor plasma obtained by centrifugation are above such diagnostic threshold, resulting in a false positive detection. The result suggests that HF-filtering greatly reduces the confounding effect due to blood cell activation facilitating biomarker detection on exosomes from parenchymal and stromal cells.

Example 7: HF-Filtering of Blood Reduces the Lipemic Index of Plasma

Figure 7:
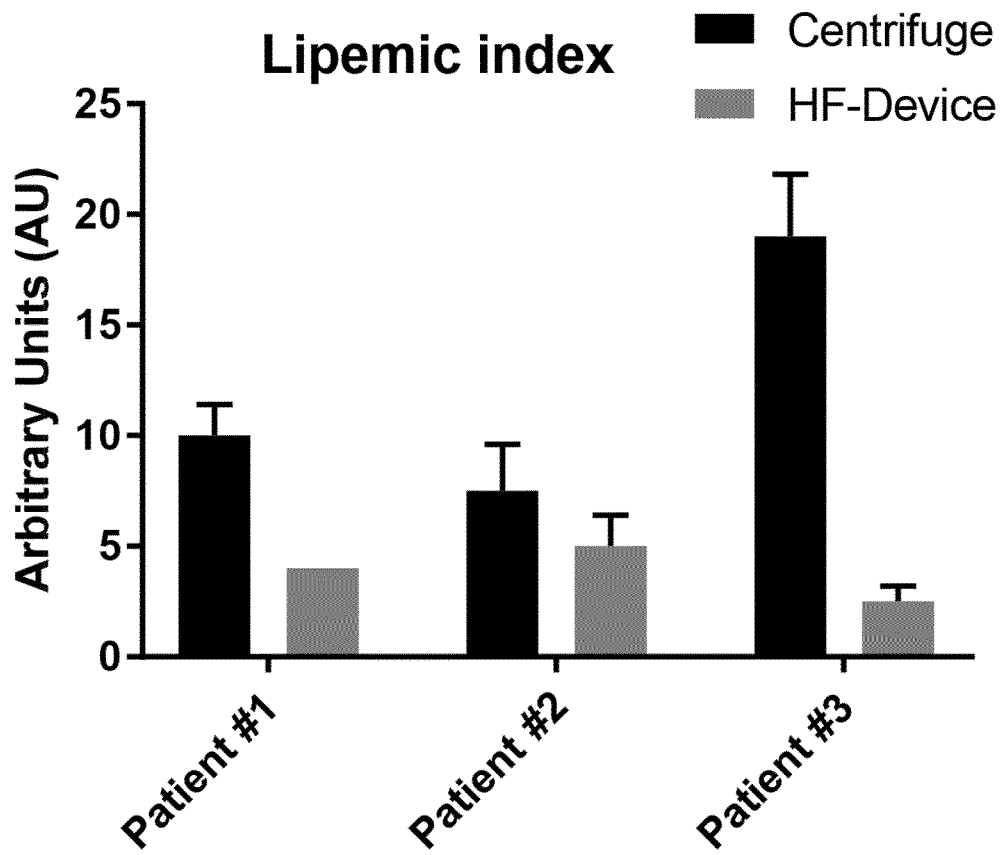
FIG. 7—Lipemic index of healthy donor plasma samples after centrifugation or filtering through 200 nm porosity polyethersulfone HF device.

FIG. 7 depicts the lipemic index of three plasma samples obtained from healthy donor blood after centrifugation or filtering through 200 nm porosity polyethersulfone HF device. The results show that HF filtering reduces the lipemic index of all three plasma samples in comparison to centrifugation. This result may be, at least in part, explained by the reduction of tryglyceride-rich chylomicrons, vesicles that have a diameter ranging from 70 nm to 1000 nm (De Haene et al.).

Figure 8:
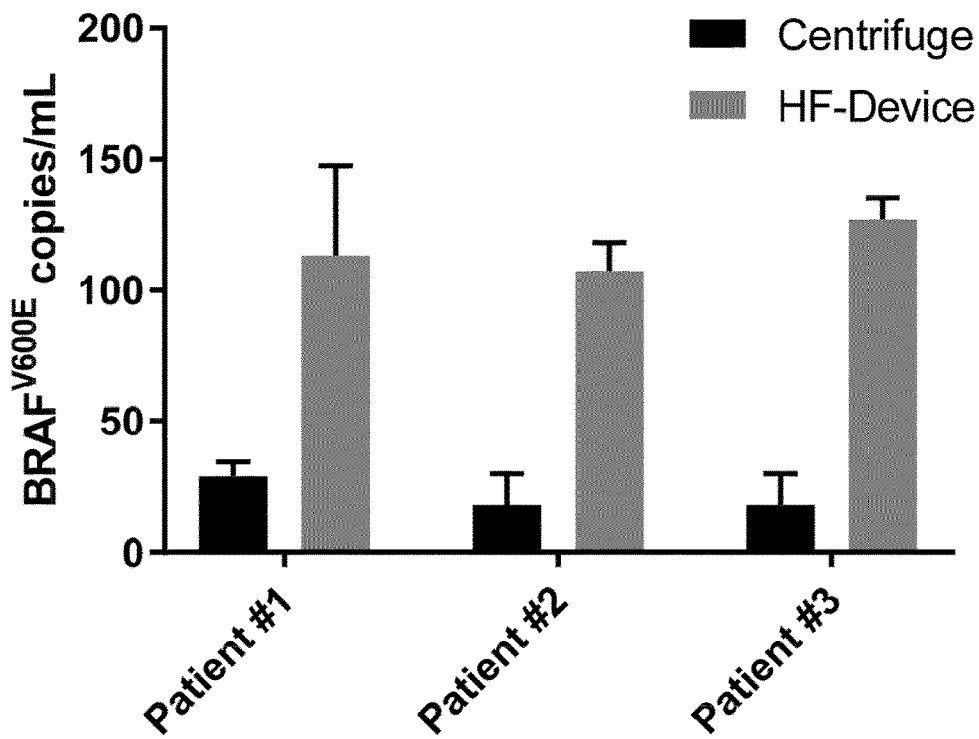
FIG. 8—Levels of $BRAF^{V600E}$ mutation copies (copies/mL) in tumour exosomes spiked in healthy donor plasma obtained by centrifugation or filtering through 200 nm porosity polyethersulfone HF device.

Example 8: Reduction of Lipemic Index by HF Filtering Improves Mutation Recovery FIG. 8 depicts the levels of BRAF$^{V600E}$ mutation copies (copies/mL) in tumour exosomes spiked in healthy fdonor plasma obtained by centrifugation or filtering through 200 nm porosity polyethersulfone HF device. The results show that more mutation copies are recovered from HF-filtered plasma than centrifuged plasma. This improved mutation recovery correlates with the observed reduction of lipemic index observed in the same set of plasma samples.

Example 9: HF-Filtering of Lipemic Plasma Samples Reduces their Lipemic Index

Figure 9:
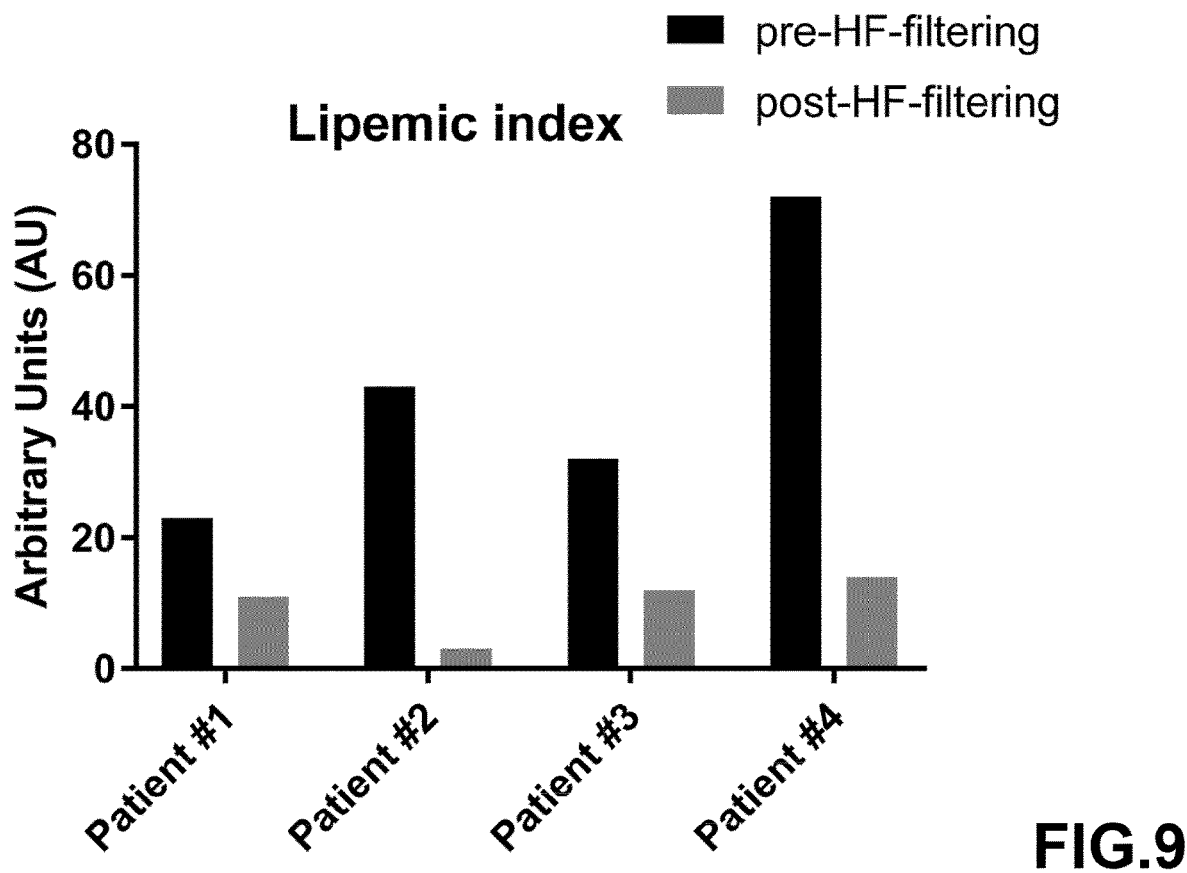
FIG. 9—Lipemic index of lipemic plasma samples before and after centrifugation or filtering through 200 nm porosity polyethersulfone HF device.

FIG. 9 the lipemic index of three lipemic plasma samples before and after centrifugation or filtering through 200 nm porosity polyethersulfone HF device. The results show that HF filtering reduces the lipemic index of all three lipemic plasma samples in comparison to centrifugation, consistent with the ability of the device to reduce the levels of tryglyceride-rich chylomicrons.

Figure 10:
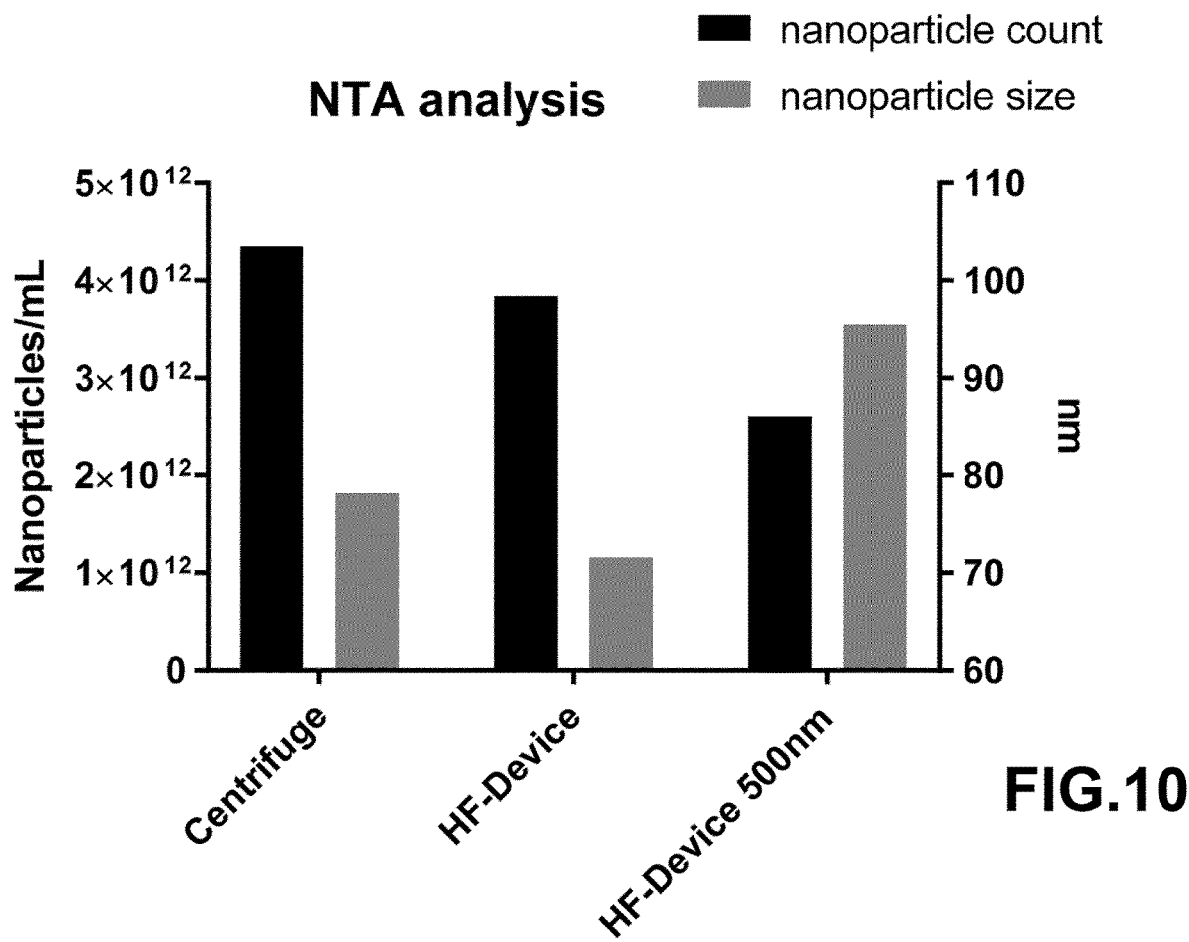
FIG. 10—Nanoparticles count of plasma obtained from whole blood using either a centrifuge, a polyethersulfone HF filter of 200 nm porosity or 500 nm porosity.

Example 10: Hollow Fiber-(HF)-Device with 500 nm Pores Efficiently Separates Nanoparticle-Rich Plasma from Blood FIG. 10. Depicts the nanoparticles count with nanotracking analysis (NTA) of plasma obtained from whole blood using either a centrifuge, a polyethersulfone HF filter of 200 nm porosity or 500 nm porosity.

It is thus shown that the HF filter with a 500 nm porosity allows to obtain a similar nanoparticles count as compared to centrifuge and HF filter with 200 nm porosity. As expected, average nanoparticle size was slightly increased by HF filter with 500 nm as compared to centrifuge and HF filter with 200 nm porosity.

Figure 11:
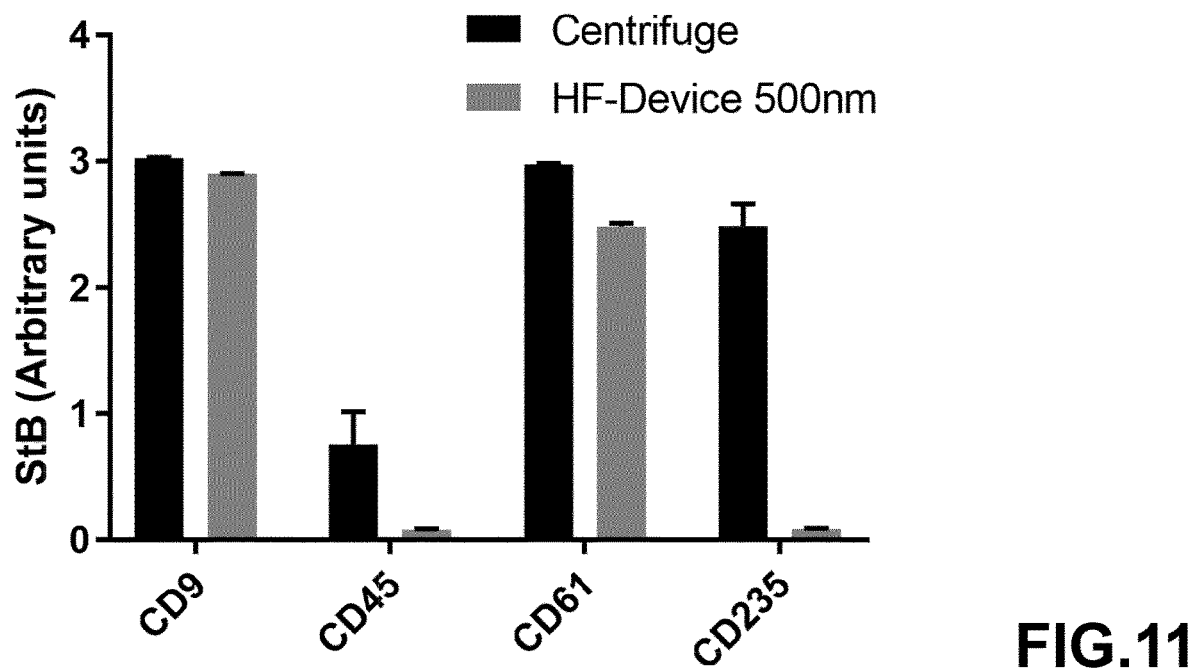
FIG. 11—Quantities of CD9-, CD45-, CD 61- and CD 235 positive exosmes measured in plasma samples obtained either by centrifugation or filtration through a 500 nm porosity polyethersulfone HF device.

Example 11: Plasma Obtained from the 500 nm HF Filtering of Whole Blood has Less Red and White Blood-Cell Derived Extracellular Vesicles than Centrifuge-Obtained Plasma FIG. 11 depicts the quantities of extracellular vesicles captured from healthy donor plasma obtained either by centrifugation or filtration through a 500 nm porosity polyethersulfone HF device using an anti-CD9 antibody (generic EV marker), an anti-CD45 antibody (generic white blood cell marker), an anti-CD61 antibody (generic platelet marker) or an an anti-CD235 antibody (generic erythrocyte marker).

It is thus shown, that the use of a 500 nm porosity polyethersulfone HF device impoverishes the sample from extracellular vesicles derived from either white blood cells and red blood cells but had no significant effect on platelet derived extracellular vesicles.

Figure 12:
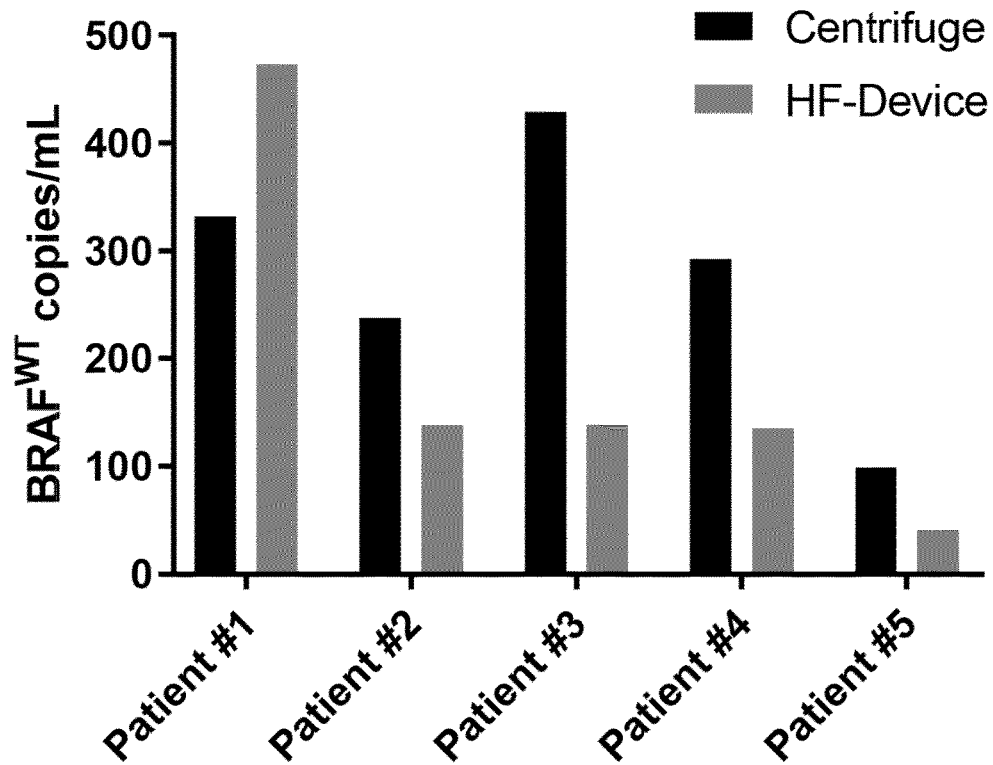
FIG. 12—Levels of wild type BRAF gene copies (copies/mL) in the plasma of metastatic melanoma patients obtained by centrifugation or filtering through 200 nm porosity polyethersulfone HF device.

Example 12: HF-Filtering Reduces the Levels of Wild Type BRAF Gene in the Plasma of Metastatic Melanoma Patients FIG. 12 depicts the levels of wild type BRAF gene copies (copies/mL) in the plasma of five metastatic melanoma patients obtained by centrifugation or filtering through 200 nm porosity polyethersulfone HF device. The results show that 4 out of five plasma samples obtained with the HF device had significantly less BRAF gene copies than those obtained by centrifugation. This result indicate that HF-filtering reduces the levels of wild type DNA in the plasma of cancer patients.

Figure 13:
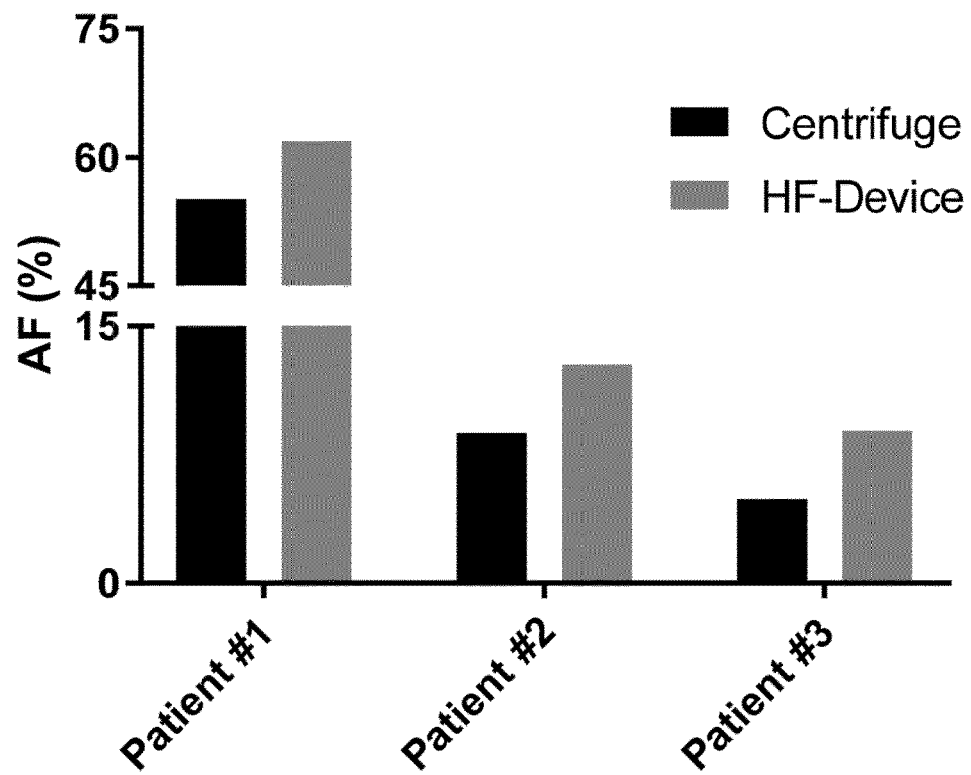
FIG. 13—Allelic frequency of BRAF gene copies (copies/mL) in the plasma of metastatic melanoma patients obtained by centrifugation or filtering through 200 nm porosity polyethersulfone HF device.

Example 13: HF-Filtering Improves the Allelic Frequency of BRAF$^{V600E}$ Mutation in the Plasma of Metastatic Melanoma Patients FIG. 13 depicts the allelic frequency of BRAF$^{V600E}$ mutation in the plasma of three metastatic melanoma patients obtained by centrifugation or filtering through 200 nm porosity polyethersulfone HF device. The results show that HF-filtering of plasma improves the allelic frequency of BRAF$^{V600E}$ in each sample. This result is consistent with the reduction of the levels of wild type BRAF gene copies observed in these samples.

Figure 14:
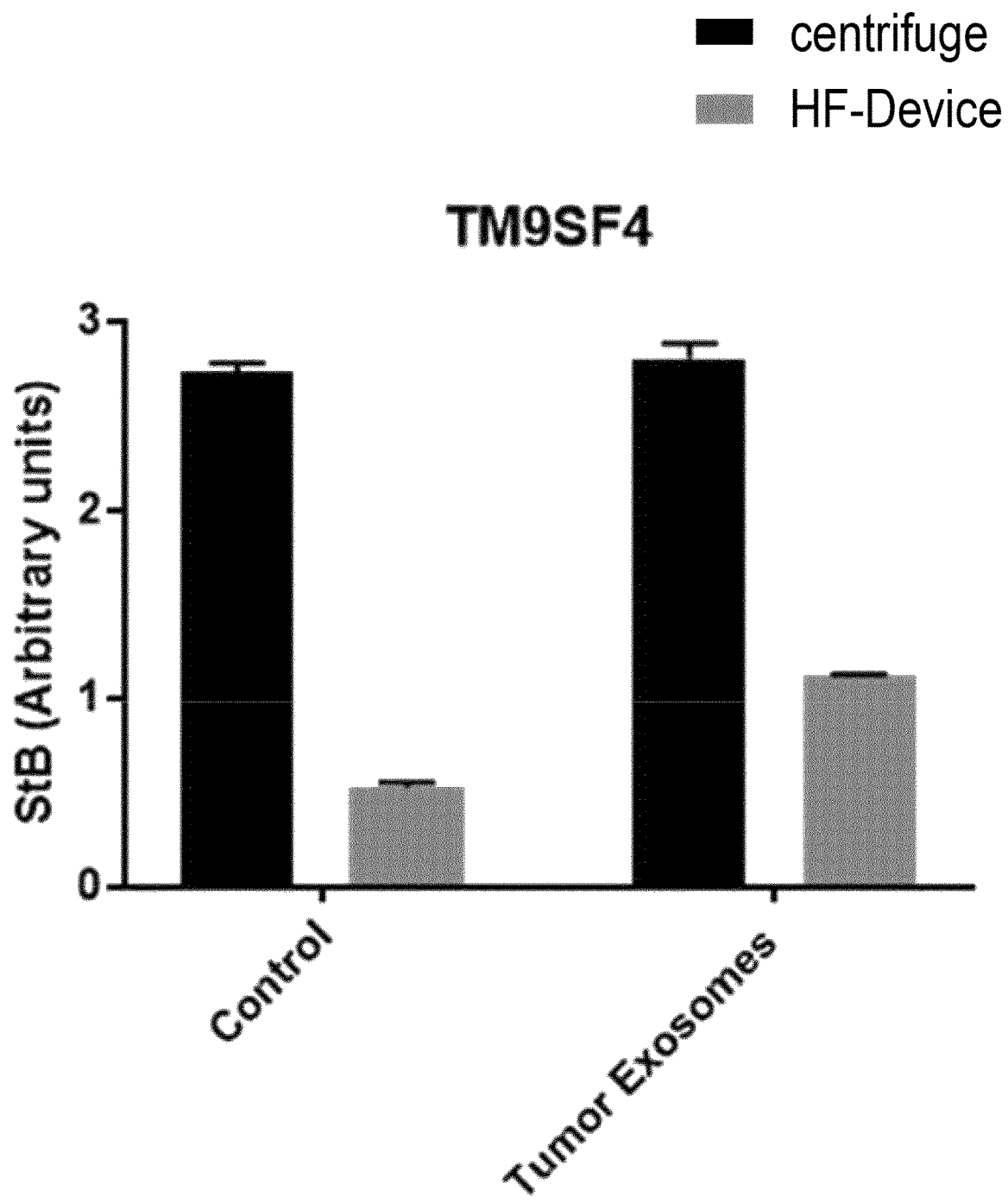
FIG. 14—Quantities of TM9SF4-positive exosomes measured in plasma samples spiked with tumor exosomes and obtained by filtration through a 200 nm HF device or by centrifugation.

Example 14: HF-Filtering with 200 nm Porosity Facilitates the Detection of Tumor Exosomes from Plasma FIG. 14 depicts the quantities of tumor exosomes captured from plasma obtained from tumor exosome-spiked blood either by centrifugation or filtration through a 200 nm porosity polyethersulfone HF device using an anti-TM9SF4 antibody, a metabolic marker expressed on exosomes derived from both tumor parenchymal and stromal cells undergoing glycolytic switch.

It is shown that the levels of TM9SF4-positive tumor exosomes increase in the plasma obtained from tumor exosome spiked blood through filtration with a 200 nm porosity polyethersulfone HF device. Conversely, no change in the levels of TM9SF4-positive tumor exosomes are observed in the plasma obtained from blood by centrifugation due to high background noise generated by blood-derived vesicles. The result suggests that HF-filtering greatly reduces the confounding effect due to blood cell activation facilitating biomarker detection on tumor exosomes.

BIBLIOGRAPHY

Black A, Pienimaeki-Roemer A, Kenyon O, Orsó E, Schmitz G Platelet-derived extracellular vesicles in plateletpheresis concentrates as a quality control approach. Transfusion. 2015 September; 55(9):2184-96.

Ishihara K, Hasegawa T, Watanabe J, Iwasaki Y. Artif Organs. 2002 December; 26(12):1014-9.

Van der Pol E, Böing A N, Harrison P, Sturk A, Nieuwland R. Classification, functions, and clinical relevance of extracellular vesicles. Pharmacol Rev. 2012 July; 64(3): 676-705.

Mock I, Membrane Processes, Vol1, Encyclopedia of Desalination and Water Resources, http://www.desware.net/Sample-Chapters/D05/D09-006.pdf Zhang H, Freitas D, Kim H S, Fabijanic K, Li Z, Chen H, Mark M T, Molina H, Martin A B, Bojmar L, Fang J, Rampersaud S, Hoshino A, Matei I, Kenific C M, Nakajima M, Mutvei A P, Sansone P, Buehring W, Wang H, Jimenez J P, Cohen-Gould L, Paknejad N, Brendel M, Manova-Todorova K, Magalhães A, Ferreira J A, Osório H, Silva A M, Massey A, Cubillos-Ruiz J R, Galletti G, Giannakakou P, Cuervo A M, Blenis J, Schwartz R, Brady M S, Peinado H, Bromberg J, Matsui H, Reis C A, Lyden D. Identification of distinct nanoparticles and subsets of extracellular vesicles by asymmetric flow field-flow fractionation. Nat Cell Biol. 2018 March; 20(3):332-343.

Lozupone F, Perdicchio M, Brambilla D, Borghi M, Meschini S, Barca S, Marino M L, Logozzi M, Federici C, Iessi E, de Milito A, Fais S. The human homologue of Dictyostelium discoideum phg1A is expressed by human metastatic melanoma cells. EMBO Rep. 2009 December; 10(12):1348-54.

Lozupone F, Borghi M, Marzoli F, Azzarito T, Matarrese P, Iessi E, Venturi G, Meschini S, Canitano A, Bona R, Cara A, Fais S. TM9SF4 is a novel V-ATPase-interacting protein that modulates tumor pH alterations asso ciated with drug resistance and invasiveness of colon cancer cells. Oncogene. 2015 Oct. 1; 34(40):5163-74.

Paolillo R, Spinello I, Quaranta M T, Pasquini L, Pelosi E, Lo Coco F, Testa U, Labbaye C. Human TM9SF4 Is a New Gene Down-Regulated by Hypoxia and Involved in Cell Adhesion of Leukemic Cells. PLoS One. 2015 May 11; 10(5):e0126968.

De Haene H, Taes Y, Christophe A, Delanghe J. Comparison of triglyceride concentration with lipemic index in disorders of triglyceride and glycerol metabolism. Clin Chem Lab Med. 2006; 44(2):220-2

Seo-Hyun Pak, Yong-Woo Jeon, Myung-Seop Shin, and Hyung Chul Koh. Preparation of Cellulose Acetate Hollow-Fiber Membranes for CO2/CH4 Separation. Environmental Engineering ScienceVol. 33, No. 1 Original Articles, Volume 369, Issues 1-2, 1 Mar. 2011, Pages 437-447

Xing Yanga, Rong Wanga, Lei Shi, Anthony G. Fanea, Marcin Debowski. Performance improvement of PVDF hollow fiber-based membrane distillation process. Journal of Membrane Science. Volume 369, Issues 1-2, 1 Mar. 2011, Pages 437-447.

Hailin Zhu, Hongjie Wanga, Feng Wanga, Yuhai Guo, Huapeng Zhang, Jianyong Chen. Preparation and properties of PTFE hollow fiber membranes for desalination through vacuum membrane distillation. Journal of Membrane Science. Volume 446, 1 Nov. 2013, Pages 145-153.

Amir Dashti, Morteza Asghari. Recent Progresses in Ceramic Hollow-Fiber Membranes. ChemBioENg Reviews.3 Feb. 2015. https://doi.org/10.1002/cben.201400014

Ze-Lin Qiu, Xin Kong, Jia-JiaYuan, Yu-Jie Shen, Bao-ku Zhu, Li-Ping Zhu, Zhi-Kan Yao, Chuyang Y. Tang. Crosslinked PVC/hyperbranched polyester composite hollow fiber membranes for dye removal. Reactive and Functional Polymers. Volume 122, January 2018, Pages 51-59

Li F S, Qiu W, Lively R P, Lee J S, Rownaghi A A, Koros W J. Polyethyleneimine-functionalized polyamide imide (Torlon) hollow-fiber sorbents for post-combustion CO2 capture. ChemSusChem. 2013 July; 6(7):1216-23.

Labreche Y, Fan Y, Rezaei F, Lively R P, Jones C W, Koros W J. Poly(amide-imide)/silica supported PEI hollow fiber sorbents for postcombustion CO(2) capture by RTSA. ACS Appl Mater Interfaces. 2014 Nov. 12; 6(21):19336-46.

Zhang Y, Zhong F, Xia S, Wang X, Li J. Autohydrogenotrophic denitrification of drinking water using a polyvinyl chloride hollow fiber membrane biofilm reactor. J Hazard Mater. 2009 Oct. 15; 170(1):203-9.

Higa M, Kakihana Y, Sugimoto T, Toyota K. Preparation of PVA-Based Hollow Fiber Ion-Exchange Membranes and Their Performance for Donnan Dialysis. Membranes (Basel). 2019 Jan. 2; 9(1). pii: E4.

What is claimed is:

1. A method for using hollow fibers for impoverishing a blood or blood-derived liquid sample from exosomes, comprising: gravity filtering the blood or blood-derived liquid sample through hollow fibers having a porosity of 200 nm to 500 nm, wherein the exosomes have a size of 30-120 nm and originate from blood components selected from the group consisting of blood red cells, blood white cells, platelets, and combinations thereof, wherein the exosomes are retained by the hollow fibers.

2. The method of claim 1, wherein the hollow fibers comprise polyethersulfone hollow fibers.

3. The method of claim 1, wherein the hollow fibers are polyethersulfone hollow fibers.

4. The method of claim 1, wherein the porosity of the hollow fibers is of about 200 nm.

5. The method of claim 1, wherein the blood-derived liquid sample is a plasma sample.

6. A method for obtaining blood or a blood derivative impoverished in exosomes originating from blood components selected from the group consisting of red blood cells, white blood cells, platelets, and combination thereof, the method comprising gravity filtering a blood or blood-derived liquid sample through a filter comprising hollow fibers having a porosity of 200 nm to 500 nm, thereby obtaining blood or a blood derivative impoverished in exosomes, the exosomes having a size of 30-120 nm.

7. The method of claim 6, wherein the hollow fibers comprise polyethersulfone hollow fibers.

8. The method of claim 6, wherein the hollow fibers are polyethersulfone hollow fibers.

9. The method of claim 6, wherein the porosity of the hollow fibers is of about 200 nm.

10. The method of claim 6, wherein the blood-derived liquid sample is a plasma sample.

* * * * *